US008589174B2

(12) United States Patent
Nelson et al.

(10) Patent No.: US 8,589,174 B2
(45) Date of Patent: Nov. 19, 2013

(54) ACTIVITY MONITORING

(75) Inventors: Kyle S. Nelson, Minneapolis, MN (US);
Brian J. Bischoff, Red Wing, MN (US)

(73) Assignee: Adventium Enterprises, Minneapolis, MN (US)

( * ) Notice: Subject to any disclaimer, the term of this patent is extended or adjusted under 35 U.S.C. 154(b) by 2369 days.

(21) Appl. No.: 10/737,076

(22) Filed: Dec. 16, 2003

(65) Prior Publication Data
US 2005/0131736 A1 Jun. 16, 2005

(51) Int. Cl.
*G06Q 50/22* (2012.01)

(52) U.S. Cl.
USPC ........................................ 705/2; 705/3; 705/4

(58) Field of Classification Search
USPC .............................. 705/2–4; 600/300; 607/60; 340/540–548
See application file for complete search history.

(56) References Cited

U.S. PATENT DOCUMENTS

| 4,777,477 | A | * | 10/1988 | Watson | 340/573.4 |
| 4,839,631 | A | * | 6/1989 | Tsuji | 340/541 |
| 5,330,513 | A | * | 7/1994 | Nichols et al. | 607/32 |
| 5,544,649 | A | * | 8/1996 | David et al. | 600/301 |
| 5,692,215 | A | * | 11/1997 | Kutzik et al. | 710/18 |
| 5,738,102 | A | * | 4/1998 | Lemelson | 600/483 |
| 5,749,372 | A | * | 5/1998 | Allen et al. | 600/595 |
| 5,751,214 | A | * | 5/1998 | Cowley et al. | 340/573.4 |
| 5,841,137 | A | * | 11/1998 | Whitney | 250/338.5 |
| 5,905,436 | A | | 5/1999 | Dwight et al. | |
| 5,967,975 | A | * | 10/1999 | Ridgeway | 600/300 |
| 5,998,780 | A | * | 12/1999 | Kramer | 250/221 |
| 6,028,514 | A | * | 2/2000 | Lemelson et al. | 340/539.13 |
| 6,108,685 | A | | 8/2000 | Kutzik et al. | |
| 6,144,954 | A | * | 11/2000 | Li | 706/62 |
| 6,280,409 | B1 | * | 8/2001 | Stone et al. | 604/67 |
| 6,440,067 | B1 | * | 8/2002 | DeLuca et al. | 600/300 |
| 6,498,652 | B1 | * | 12/2002 | Varshneya et al. | 356/477 |
| 6,523,009 | B1 | * | 2/2003 | Wilkins | 705/3 |
| 6,524,239 | B1 | | 2/2003 | Reed et al. | |
| 6,544,200 | B1 | * | 4/2003 | Smith et al. | 600/595 |
| 6,582,380 | B2 | * | 6/2003 | Kazlausky et al. | 600/595 |
| 6,614,348 | B2 | * | 9/2003 | Ciccolo et al. | 340/541 |
| 6,821,258 | B2 | | 11/2004 | Reed et al. | |
| 6,888,457 | B2 | * | 5/2005 | Wilkinson et al. | 340/540 |

(Continued)

FOREIGN PATENT DOCUMENTS

DE 195 22 803 1/1997

OTHER PUBLICATIONS

AIST, "Housing that Protects the Home-maker—Development of Technology Capable of Detecting Abnormalities in the Ordinary Living Pattern of the Home-maker for Information Signaling and Health Management—", http//www.aist.go.jp/aist_e/latest_research/2003/20030221/20030221.html, AIST, 10 pgs. (Feb. 3, 2003).

*Primary Examiner* — Lena Najarian
*Assistant Examiner* — Teresa Woods
(74) *Attorney, Agent, or Firm* — Brooks, Cameron & Huebsch, PLLC

(57) ABSTRACT

Embodiments of the present invention relate to methods, devices, and systems to monitor activity. One method to monitor activity includes monitoring a sensor activated by an individual. The method also includes recording activation of the sensor, determining a behavior routine of the individual based on recorded activations of the sensor, and analyzing the recorded sensor activations to determine a behavior routine. The method also includes identifying a change in the behavior routine based on the analysis of the recorded sensor activations.

35 Claims, 10 Drawing Sheets

(56) References Cited

U.S. PATENT DOCUMENTS

| | | |
|---|---|---|
| 6,957,107 B2 * | 10/2005 | Rogers et al. .................. 607/60 |
| 2002/0169583 A1 | 11/2002 | Gutta et al. |
| 2002/0198473 A1 | 12/2002 | Kumar et al. ................. 600/595 |
| 2003/0004652 A1 | 1/2003 | Brunner et al. |
| 2003/0114763 A1 | 6/2003 | Reed et al. .................... 600/300 |
| 2003/0117279 A1 | 6/2003 | Ueno et al. .................... 340/523 |
| 2003/0130590 A1 | 7/2003 | Bui et al. ....................... 600/537 |
| 2003/0189485 A1 | 10/2003 | Smith ........................... 340/540 |
| 2003/0229471 A1 | 12/2003 | Guralnik et al. |
| 2004/0015132 A1 * | 1/2004 | Brown ........................... 604/131 |

* cited by examiner

| MORNING ACTIVITY | COUNTS | THRESHOLD FOR ACTIVITY |
|---|---|---|
| BEDROOM | 5 | 4 |
| BATHROOM | 10 | 5 |
| KITCHEN | 15 | 5 |
| DINING ROOM | 2 | 0 |
| LIVING ROOM | 2 | 0 |
| LAUNDRY ROOM | 0 | 0 |
| TOTAL COUNTS 34 | | TOTAL THRESHOLD 14 |

*Fig. 3A*

| AFTERNOON ACTIVITY | COUNTS | THRESHOLD FOR ACTIVITY |
|---|---|---|
| BEDROOM | 0 | 0 |
| BATHROOM | 2 | 0 |
| KITCHEN | 10 | 5 |
| DINING ROOM | 2 | 0 |
| LIVING ROOM | 4 | 0 |
| LAUNDRY ROOM | 2 | 0 |
| TOTAL COUNTS 20 | | TOTAL THRESHOLD 5 |

*Fig. 3B*

| EVENING ACTIVITY | COUNTS | THRESHOLD FOR ACTIVITY |
|---|---|---|
| BEDROOM | 5 | 0 |
| BATHROOM | 10 | 5 |
| KITCHEN | 15 | 5 |
| DINING ROOM | 2 | 0 |
| LIVING ROOM | 2 | 0 |
| LAUNDRY ROOM | 0 | 0 |
| TOTAL COUNTS 34 | | TOTAL THRESHOLD 10 |

*Fig. 3C*

| NIGHT TIME ACTIVITY | COUNTS | THRESHOLD FOR ACTIVITY |
|---|---|---|
| BEDROOM | 3 | 1 |
| BATHROOM | 4 | 0 |
| KITCHEN | 2 | 0 |
| DINING ROOM | 0 | 0 |
| LIVING ROOM | 0 | 0 |
| LAUNDRY ROOM | 0 | 0 |
| TOTAL COUNTS 9 | | TOTAL THRESHOLD 1 |

*Fig. 3D*

| SENSORS GROUPED BY ACTIVITIES OF DAILY LIVING | COUNTS | THRESHOLDS |
|---|---|---|
| WAKING (BEDROOM, BATHROOM) | 15 | 7 |
| BREAKFAST (KITCHEN, DINING ROOM) | 17 | 8 |
| MORNING ACTIVITY (ALL SENSORS) | 6 | 1 |
| LUNCH (KITCHEN, DINING ROOM) | 12 | 6 |
| AFTERNOON ACTIVITY (ALL SENSORS) | 16 | 2 |
| DINNER (KITCHEN, DINING ROOM) | 19 | 8 |
| PREPARE FOR BED (BEDROOM, BATHROOM) | 7 | 2 |
| TOTAL COUNTS | 92 | TOTAL THRESHOLD 34 |

*Fig. 4*

THIRD PARTY CALL HIERARCHY AND INFORMATION TO BE PROVIDED

| CALL # | CONTACT | INFORMATION |
|---|---|---|
| 1 | INDIVIDUAL | ARE YOU O.K.? |
| 2 | NEIGHBOR | NAME, REQUEST TO CHECK, PHONE # |
| 3 | RELATIVE | NAME, REQUEST TO CHECK, ADDRESS, PHONE # |
| 4 | DOCTOR | NAME, TIME AND OBSERVED CHANGE, ADDRESS, PHONE # |
| 5 | EMERGENCY | NAME, TIME AND OBSERVED CHANGE, MEDICAL HISTORY INFORMATION, LIST OF CONTACTS ATTEMPTED, ADDRESS, PHONE # |

*Fig. 6*

ACTIVITY MONITORING

This invention was made with government support under Grant Number 1R41AG022751-01 awarded by the National Institute on Aging. The government has certain rights in the invention.

BACKGROUND OF THE INVENTION

In the field of remote health monitoring, systems have been developed to enable an individual to contact medical professionals from their dwelling regarding a medical emergency. For example, in various systems, an individual is equipped with an emergency call button that initiates a call or signal to an emergency call center. The concept of such a system is that if an individual has a health related problem, they can press the emergency call button and emergency medical providers will respond to assist them. However, in some cases, the individual is unable to press the emergency call button, such as when an individual has fallen and cannot reach the button or is rendered unconscious.

More complex systems have also been designed to monitor medication compliance or check health characteristics of an individual, such as heart rate, body temperature, blood chemistry, blood pressure, respiration, and the like. In these systems, the individual typically has to provide data periodically, such as by telephoning a monitoring center to provide health information to the center or by checking onto a web site or other data collection system. For example, blood chemistry monitoring systems have been devised where an individual takes a sample of their blood, performs tests on the blood, and provides the results to medical professionals via a telephone line. The blood chemistry information is then reviewed by a medical professional in order to monitor the health of the individual.

Neither of the above systems has the capability to automatically detect if someone has become incapacitated and requires assistance. There are numerous For example, in various embodiments, a monitoring system can monitor the activities within a dwelling and can provide automated alerting to a number of third parties selected by the individual that can render assistance. Some embodiments can incorporate an emergency calling feature with an automated detection feature to detect if an individual has become incapacitated and to initiate a call to emergency personnel. Embodiments include systems to monitor the activity of an individual within a dwelling, such as a house, condominium, townhouse, or apartment.

Embodiments of the invention include a number of sensors that are connected to a variety of items within the dwelling to indicate the activity of the individual. For example, sensors can be connected to the user's bed to indicate that a user is lying on the bed. Sensors can also be used on drawers and cupboards to indicate when the individual opens a drawer or the door to a cupboard. Many other types and uses for the sensors are described in more detail below. Various embodiments of the invention are designed to be transparent to the occupant of the dwelling and, therefore, such a system can monitor the daily routine of the occupant without the occupant having to interact with the system, such as by logging onto websites, entering health data, and the like.

Additionally, by using the information from the sensors, the system can identify the activity of the individual being monitored. The system can also track user behavior over time and can create expected amounts of activity and types of activity during certain periods of time. For example, in various embodiments of the system, the system can monitor sensors that indicate that the individual is eating, such as by tracking activations of sensors in the kitchen and the dining room. If tracked over a number of days, weeks, months, or even years, this information can be analyzed to identify a behavior routine.

The information can be analyzed to identify if there is a usual pattern of activity or number of sensor activations that are indicative of the individual doing accounts of such individuals that have been in distress for periods of hours or days after they have fallen or become ill and have not been able to sunmmon help, especially with respect to elderly individuals living alone.

BRIEF DESCRIPTION OF THE DRAWINGS

FIG. 3A illustrates an embodiment for monitoring morning activity.

FIG. 3B illustrates an embodiment for monitoring afternoon activity.

FIG. 3C illustrates an embodiment for monitoring evening activity.

FIG. 3D illustrates an embodiment for monitoring nighttime activity.

FIG. 4 illustrates an embodiment for monitoring daily activity.

FIG. 6 illustrates an embodiment of a calling hierarchy.

DETAILED DESCRIPTION OF THE INVENTION

Embodiments of the present invention can provide simple, cost effective, non-intrusive methods, devices, and systems for monitoring activity. Embodiments can provide automated detection of changes in activity within a dwelling and initiation of alerts to third parties to check on and/or assist the individual where assistance is needed, thereby avoiding prolonged periods of time before assistance is provided. an activity, such as eating. By tracking patterns of activity, the system can interpret when there is a statistical deviation in the behavior routine of the individual. A deviation in an analysis of a short period of time, such as hours, days, or weeks, may be an indicator, for example, that the individual is having a heath related problem. For instance, deviations can indicate that an individual has fallen or is incapacitated.

The tracked pattern information can also be analyzed over a long period of time, such as months or years, to aid in the diagnosis of the emergence of a health related issue. For example, the data can indicate that an individual is sleeping more or less, eating more or less, or toileting more or less, each of which can be symptomatic of an emerging health condition.

Embodiments of the invention can provide several types of alert triggers. For example, alert triggers can include an emergency switch/button, inactivity with the occupant believed to be home, and persistent (unusual) activity from one or more sensors (e.g., waving hand in front of a motion sensor after falling). In various embodiments, a confidence level can be created based upon the number of sensors that are indicating a change in the activity of the individual. For example, if one sensor is signaling abnormal behavior, but the other sensors in its group are recording normal behavior, the confidence level of the abnormal behavior could be assigned a low level. Whereas, when all sensors within a group are recording abnormal behavior, then the confidence level could be deemed to be high.

With respect to cases such as inactivity with the occupant believed to be home, and persistent activity from one or more sensors, program instructions can monitor the activity of an individual to identify changes in a behavioral routine. For example, when many people go about their daily activities, the activation of sensors can occur in localized bursts (e.g., a burst of activity in the kitchen or a burst in the bathroom). In such cases, an activity can be considered as being started when a first count is received by the monitoring device. As stated above, a record can be kept of the counts for that activity. If a count is received from a sensor in a different group, the current activity can be ended (with the end time being the time of the last count) and a new activity can be created with the start time being the currently received count.

Figure 1:
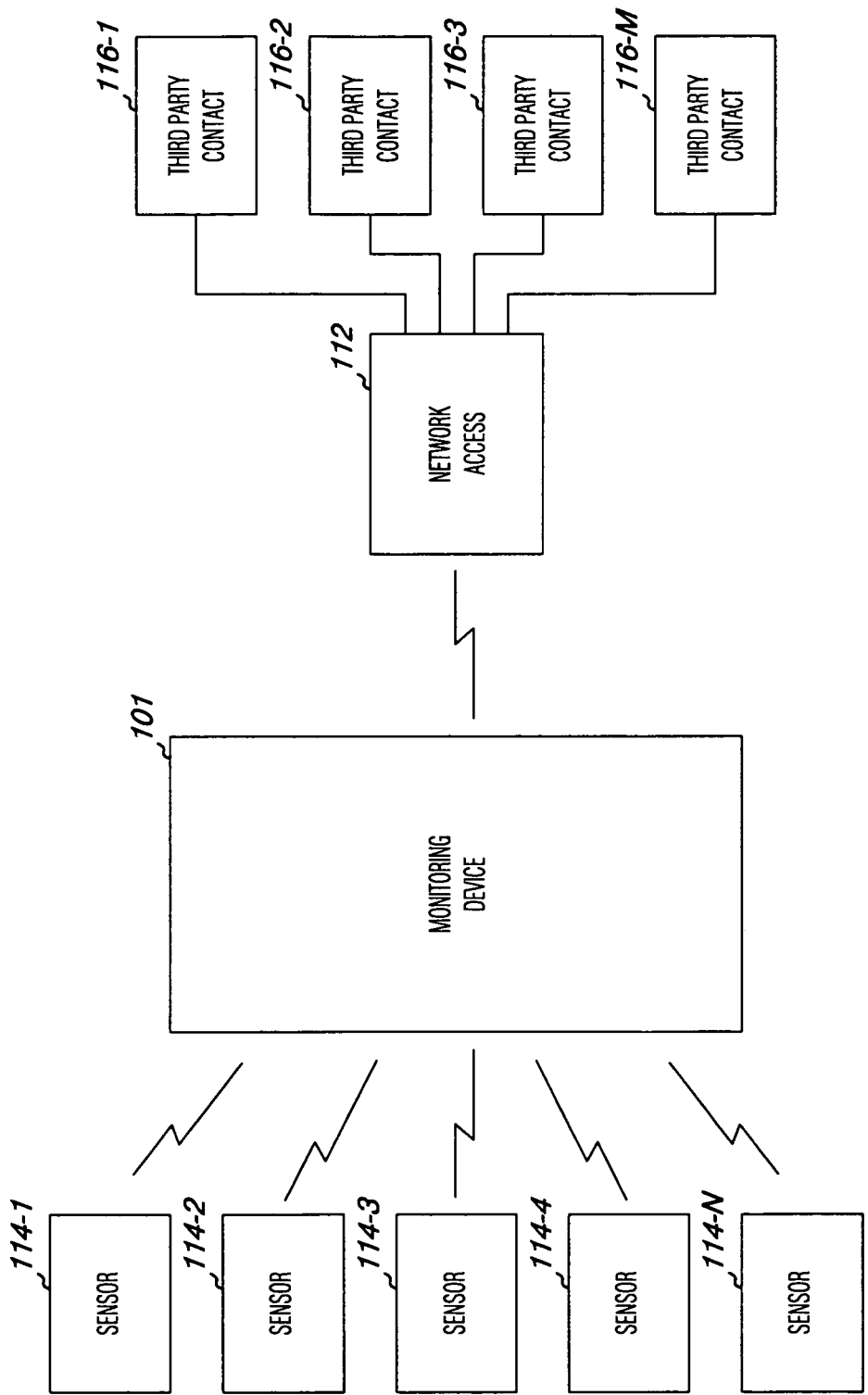
FIG. 1 illustrates an activity monitoring system embodiment.

FIG. 1 illustrates an activity monitoring system embodiment. In the embodiment shown in FIG. 1, the system includes a monitoring device 101, network access point 112, a number of sensors 114-1 through 114-N, and a number of third party contacts 116-1 through 116-M. The letters M and N have been chosen to indicate that embodiments can have various numbers of sensors/third parties. As used herein, M and N can be any number and M can be a number identical to or different from N.

The monitoring device 101, as discussed in more detail below, includes program instructions to receive signals from the sensors 114-1 through 114-N that are generated by activation of a sensor, such as sensor 114-1. In various embodiments, signals are generated in a binary (or on/off) fashion, such that the sensor generates a signal when the object being sensed changes state. For example, with respect to a sensor on a door, one type of sensor that can be provided can operate such that when the door is closed, no signal is generated, but when the door is opened, a signal is generated. Similarly, when the door is closed again, another signal may be generated. Since the signals are either on or off, the signals are typically easy to track and the sensors are inexpensive. However, embodiments of the invention are not limited to the use of on/off type sensors.

The program instructions of the monitoring device 101 can also track signals related to a sensor, e.g. 114-1, and/or a group of sensors, such as sensors 114-1 through 114-3. The tracking of the signals can be accomplished by counting the number of signals received from a sensor by the monitoring device 101. The received signals are generally referred to herein as "counts".

As shown in the embodiment of FIG. 1, the system includes one or more sensors. For example, in the embodiment of FIG. 1, five sensors are shown. The sensors can be of various types, for example, types of sensors include: sensors to indicate the opening and closing of a door or drawer; sensors to indicate the movement of objects such as shades or blinds; current and/or voltage sensors to monitor appliances, lights, wells, etc.; pressure or fluid flow sensors to indicate the turning on and off of water; temperature sensors to indicate that the furnace is on or off; force sensors such as strain gauge sensors to sense an individual walking over a pad, sitting in a chair, or lying in bed; motion sensors to sense the motion of objects within the dwelling; and alert switches/buttons to signal an emergency. The sensors can be either analog or digital type sensors and can include program instructions to transmit Boolean logic output to the monitoring device. In this way, the monitoring device can receive signals represented in formats such as on/off or 0/1 outputs. However, the embodiments of the invention are not limited to the above types of sensors or the above uses for the sensors.

Those skilled in the art will understand that the various sensors can transmit their signals in any manner and that various sensors can transmit signals in different ways. For example sensors can transmit signals by radio frequency, infrared, acoustic, optical, and/or electrical signaling (e.g., power line carrier and hardwired), among other modes of transmission.

Based upon the tracking of counts created by the activation of a sensor, program instructions can be provided to the monitoring device 101 to analyze the numbers of counts tracked by the monitoring device 101. For example, the analysis of the counts can be used to calculate expected numbers of counts for a particular sensor during a period of time. This analysis can also be done for a group of sensors, such as a group of sensors associated with an activity of daily living, for example. Activities of daily living can be characterized as any activity, of an individual, that can be sensed by the sensors of the various embodiments of the invention. Other examples of groupings of sensors include sensors within a room or sensors grouped by function or type of sensor, among others.

In various embodiments, analysis can compare the tracked counts to one or more thresholds. Thresholds can be used to indicate when a statistical change in the number of counts has deviated to a point where an alert should be initiated. The thresholds can be preset, set by the system, or input into the system during or after installation of the system into a dwelling. Those skilled in the art will understand that any triggering mechanism can be used to trigger an alert and that the embodiments of the present invention are not limited to the use of thresholds.

The monitoring device 101, can also provide behavior routines that include a number of thresholds for making comparisons to the tracked counts. Thresholds can be used to trigger an alert in which a call to the individual and/or to one or more third parties 116-1 to 116-M, via a network access point 112, is initiated. The third parties 116-1 through 116-M include parties such as a neighbor, a relative, a doctor, an emergency contact, and/or monitoring system repair personnel, among others.

A call can be initiated, for example, based upon the analysis including a comparison of the received counts to a threshold as will be described more fully below. The network access point 112 can provide a path for the monitoring device 101 to communicate a message to a third party, such as third party 116-1. For example, a Public Switched Telephone Network (PSTN) and a Mobile Switching Center (MSC) are two examples of network access points 112 that can be used with respect to embodiments of the invention. However, the embodiments of the invention are not so limited.

Figure 2A:
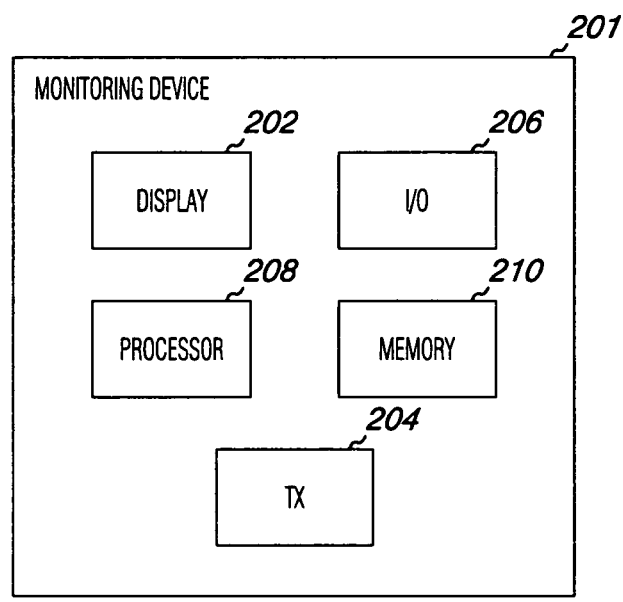
FIG. 2A illustrates a monitoring device embodiment.

FIG. 2A illustrates a monitoring device embodiment. In the embodiment of FIG. 2A, the monitoring device 201 includes a display 202, a transceiver 204, an Input/Output (I/O) device 206, a processor 208, and memory 210.

The display 202 can provide a number of functions. For example, the display 202 can be used to aid in the set-up of a monitoring system, such as the monitoring system shown in FIG. 1, by showing set-up instructions thereon. In this way, a person installing the monitoring system can follow the instructions and when finished can use the I/O device 206 to signal the monitoring system to move on to the next step of the set-up process. As shown in FIG. 2A, an I/O device 206, such as a touch screen, speaker/microphone, and/or keypad, can be provided to allow the monitoring system to be configured by entering information therein. In some embodiments, the monitoring system can communicate with a set-up device (not shown) that can aid in setting up the monitoring system. Examples of set-up devices include personal computers and hand-held devices, such as personal digital assistants and the like, among others. The monitoring system can communicate with a set-up device in various manners, such as through the PSTN, a cellular telephone network, or an I/O connection to a device or network, among others.

Additionally, the display 202 and the I/O device 206 can be used together to provide various functions. For example, questions or blanks for data to be input can be presented on the display 202 and the I/O device 206 can be used to input information into the monitoring device 201 in response to the question shown on the display 202 or to fill in the blanks provided on the display 202.

The processor 208 can operate on computer executable instructions as part of the control logic for controlling operations of the monitoring device 201. Computer executable instructions can be stored in the memory 210 and executed by the processor 208. Memory can also be used to store data used in embodiments of the invention, such as sensor activation counts, grouping of activities, trend information, and the like. Memory, as referred to herein, can include non-volatile and volatile memory such as read only memory (ROM) and random access memory (RAM), including flash memory and optical memory, among others. Those skilled in the art will understand that data stored in memory and signals from the sensors can include security features, such as encryption, to maintain the privacy of the information in case of theft or other such circumstances.

The monitoring device 201 can be a stand alone unit that is independent of other devices in the dwelling. The monitoring device 201 can also be incorporated or combined with various other household devices. For example, the monitoring device 201 can be combined with another household device, such that the combined unit provides additional functionalities such as a radio, a clock radio, an alarm clock, a telephone, or an answering machine, among others. In this way, the monitoring device component of the monitoring system is presented in a non-intrusive manner into the individual's life.

Figure 2B:
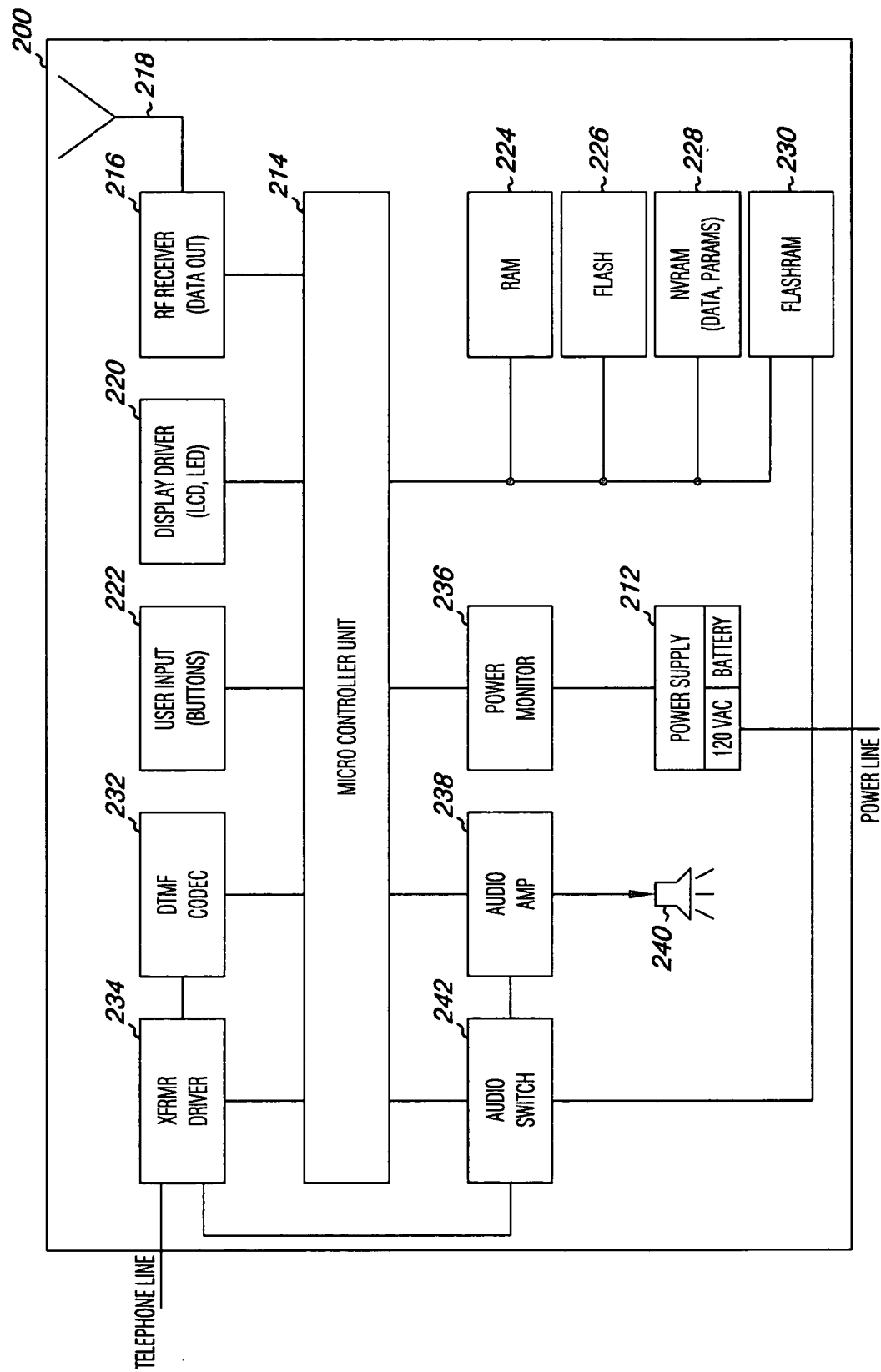
FIG. 2B illustrates another monitoring device embodiment.

FIG. 2B illustrates another monitoring device embodiment. In the embodiment of FIG. 2B, the monitoring device 200 generally includes a power supply 212, a micro controller unit 214, and a receiver 216.

The power supply 212 provides power to the device 200. The power supply 212 can be connected to a wired power source entering the dwelling and/or can be operable using batteries. The monitoring device 200 can include a power monitor 236 that can monitor the amount of power available, available power sources, what power source is being used, and/or indicate that a power source has to be attended to, such as by indicating that the battery power is low or that batteries should be installed or changed.

The micro controller unit (MCU) 214 can be used to control the functions of the monitoring device 200. For example, the MCU 214 can include program instructions such functions as handling received information from the sensors in the monitoring system and analyzing the count data, among others. A MCU can include RAM and/or ROM, a clock, an input/output, and a processor.

As shown in FIG. 2B, the monitoring device 200 can also include one or more types of memory (e.g., RAM 224, flash 226, non-volatile RAM 228, flash RAM 230, among others). This memory can be used to provide storage for various information, as described above with respect to memory 210 of FIG. 2A.

The monitoring device 200 also can include a receiver or transceiver for receiving signals from the various sensors of the monitoring system. For example, a RF receiver 216 connected to an antenna 218, as shown in FIG. 2B, is one type of receiver. In the embodiment of FIG. 2B, a display driver 220 has been provided to execute instructions regarding the functioning of a display such as an LCD or LED display resident on the monitoring device 200. The monitoring device 200, can also include a user input 222, such as a keypad and/or microphone to receiver.

A speaker 240, an audio amp 238, and an audio switch 242 can also be included in the monitoring device 200. The speaker 240 is provided, for example, to provide an alert to the individual, among other functions. The audio switch 242 can be used when the monitoring device 200 initiates an audio alert either to an individual (e.g., through speaker 240) or to a third party (e.g., via the telephone line).

The monitoring device 200 can also include a coder-decoder 232 and transformer driver 234. The coder-decoder 232 can be a dual tone multi-frequency (DTMF) coder-decoder, such as that shown in FIG. 2B. The coder-decoder 232 converts analog signals to digital code and vice versa. This enables the monitoring device 200 to, for example, store telephone numbers in memory as digital code and change the code into audible telephone dialing sounds to dial the telephone number.

The transformer driver 234 can be used to feed audio output to a telephone line. For example, a message can be recorded, stored in memory, and when an alert is initiated, sent through the transformer driver 234 to the telephone line. The transformer driver can also be used to adjust the volume and/or sound quality of a message.

FIGS. 3A-3D illustrate a method of monitoring activity. FIG. 3A illustrates activity during a period classified as the morning. FIG. 3B illustrates activity during a period classified as the afternoon. FIG. 3C illustrates activity during a period classified as the evening. FIG. 3D illustrates activity during a period classified as nighttime. In the embodiment shown in FIGS. 3A-3D, each period encompasses 6 hours of the day. However, the invention is not so limited.

FIG. 3A illustrates an embodiment for monitoring morning activity. In FIG. 3A, the activations of sensors in each room of the dwelling have been tracked and are shown. In the embodiment shown in FIGS. 3A-3D, the counts and threshold amounts have been tracked according to each group of sensors within a particular room and a total number of counts and total threshold have been computed. In this way, this data can be used to trigger alerts based upon the statistical change in counts of the total period of time or can be used to trigger an alert based upon the statistical change of one or more of the groups of sensors.

In various embodiments, a number of low and/or high thresholds can be used to trigger the initiation of an alert. In the embodiment shown in FIG. 3A, a single low threshold is used. A low threshold can be used to identify activity levels that are below a threshold of normal levels. Low levels can indicate, for example, that an individual has become immobilized or incapacitated. Conversely, high thresholds can be used to identify activity levels that are above a threshold of normal levels. High levels can indicate that an individual is using the sensor to try to signal that they are in need of assistance, for example, by repeatedly opening and closing a door on a cabinet. In the embodiment shown in FIG. 3A, the counts of each room for the morning period are all greater than the threshold amount. Since a low threshold is used, an alert will not be triggered.

Program instructions within a monitoring device can be used to analyze the data to determine when to trigger an alert. For example, the program instructions can analyze a number of counts from a room, e.g., bedroom, by comparing the number of counts that were signaled by the sensors within the bedroom to an expected threshold for activity. It is understood, however, that the sensors can be grouped into groups that are smaller than all of the sensors in a room and that sensors can be tracked independently from the other sensors.

In the example shown in FIG. 3A, the bedroom recorded five counts from sensors in the bedroom, with the threshold set at four. The number of sensor counts is greater than the threshold amount and, therefore, in the embodiment of FIG. 3A, the activity shown is considered normal activity. Alternatively, if the number of sensor counts is lower than the threshold, it can be interpreted to indicate abnormal activity.

Since there can be many reasons for abnormal activity, program instructions can use information from other sensors to provide additional certainty before the monitoring device initiates alerts and calls to third parties. For example, the individual has an appointment in the morning and rushes to get ready. In this instance, perhaps only three counts are recorded in the bedroom and only three counts are sensed in the bathroom. In this case, program instructions will identify that the numbers of counts for those rooms are less than the thresholds for their respective rooms.

The program instructions can be designed to trigger an alert based upon a statistical change that is below the threshold in the case of one or both rooms, or the program instructions can use additional data to further identify whether an alert should be triggered. Various types of additional information can be used to provide additional certainty to the determination of whether an alert should be initiated. For example, other information that can be taken into account can be the count total from other rooms, the total count total for the period, whether the individual is still within the dwelling, number of counts in previous time periods, or waiting for the next time period to receive more information and using that information to further analyze whether an alert should be triggered, among others.

For example, FIG. 3B illustrates an embodiment for monitoring afternoon activity. If the activity in the afternoon period has returned to above threshold levels, then there is no immediate need for an alert. However, in some embodiments, the statistical changes that fell below the threshold can be recorded and used for analysis of long term changes in activity.

This information can also be used to adapt the expected levels of sensor counts. This allows the monitoring system to learn the routine of the individual and adapt its thresholds to better mirror the routine of the particular individual the system is monitoring. For example, if the individual always has a meeting during the week and rushes to get ready resulting in counts that are below the threshold, then the program instructions in the system can review the recorded statistical changes to identify if there is a better fit threshold than the threshold that is being applied.

In order for the program instructions to be able to adapt, a probabilistic approach to problem solving can be employed, e.g. through use of Bayesian or other such decision theories. For example, starting with the general behaviors within an individual's routine, such as things like eating, sleeping, toileting, etc., a compositional model of behavior can be created.

A behavior template that models the behavior of the individual can be created for each general behavior. The behavior template can be parameterized so that individual variances can be accommodated and adjusted after installation. For example, the initial time periods for expected behaviors will be largely undefined at installation, but as data about the counts from the sensors is acquired and analyzed, and conclusions reached by the program instructions, the time periods (and other parameters) will be gradually adjusted to more accurately represent the routine of the individual. In addition to understanding generally when an event, such as waking, will take place, the sensors that are activated can provide low level detail about what the individual is actually doing. For example, when a number of counts are received from sensors in the kitchen, it can be assumed that the individual is preparing to eat.

Additionally, the particular sensors can each be individually identifiable in various embodiments which can allow for a level of detail such as: the individual turned on the light, went to the cupboard where the glasses are kept, then to the cupboard with the plates, then to the drawer with the silverware, then to the refrigerator, and this procedure took 3.25 minutes. The light was then turned off 15 minutes later. This information can be helpful in many ways. For example, the time and distance to achieve the same tasks, when monitored over a long period of time, can help to indicate whether the individual's mobility is beginning to be impaired, based on the time to achieve the tasks slowing over time.

Recorded low level details, such as appliance usage, can be composed into more complex and, consequently, more informative behaviors. The low level details can contain information including the start and stop time of the behavior and other data relevant to the behavior (e.g., location). The low level details can be used with Boolean decision theory (e.g., true/false or yes/no) such that it can be determined whether or not the behavior was observed.

Certain sensor behaviors can also indicate behaviors that are better indicators of an individual having a health problem. For example, if sensor activity indicates that the shower has been running for a prolonged period, it may be an indication that the individual is unable to turn off the shower and therefore, outside assistance may be necessary. Such functionality can be provided by the program instructions of the monitoring device.

Additionally, since most people do not do exactly the same thing everyday, a standard deviation can be used with the one or more thresholds. In this way, the thresholds are not discrete lines that are crossed, but rather there is a range of acceptable counts for each sensor and/or group of sensors.

FIGS. 3C and 3D illustrate embodiments for monitoring activity during an evening and a night time period. These Figures illustrate that thresholds can be different for each time period, since people are typically not in the same place all day and typically do different things at different times of day. In various embodiments, the monitoring device can be designed to have default thresholds such that when the monitoring system is initially set up, the alert functionality is functional. In various embodiments as discussed above, the program instructions of the monitoring device can track the received counts and can learn from the patterns within the tracked count data to learn about the behavior routine of the particular individual being monitored and can adjust the thresholds based on the behavior routine.

The system can also include program instructions to provide a self-diagnostic functionality to assess whether the system is functioning properly, optimally, and/or the like. For example, the monitoring system can ascertain whether a sensor has been moved to a different group without being reassigned. For example, if a sensor from the kitchen has been moved to the bedroom, when the individual is in the bedroom, movement may be indicated as occurring in both the bedroom (i.e., by the other sensors in the room) and in the kitchen (i.e., by the sensor that has been moved but not reassigned). Through use of the self-diagnostic functionality, the incorrect positioning of sensors can be identified and a request to reposition the sensor can be made to the individual or to system repair personnel.

In various embodiments, program instructions within a monitoring device can also use a self-diagnostic functionality to analyze the sensor data to determine when the monitoring device, the monitoring system, or a sensor is malfunctioning or is not operational. For example, the program instructions can analyze a number of counts from a sensor within a group, such as a room, and can identify a deviation from a normal routine based on the change in counts that were received from the sensor. If an abnormally low or high number of counts, for example, are received, the monitoring system can check other sensors within the room to see if they are signaling activity, and can identify if the activity of the other sensors is consistent with the behavior routine.

If the other sensors are signaling normal behavior, the monitoring system can continue to monitor the sensor, signaling abnormal behavior, to further confirm that it is malfunctioning or inoperative, or can initiate an alert to the individual and/or monitoring system repair personnel to check the sensor. Those skilled in the art will understand that in various embodiments, the monitoring device can diagnose problems within the monitoring system in various manners and can initiate alerts to the individual and/or repair personnel based upon the diagnosis.

FIG. 4 illustrates another embodiment for monitoring daily activity. FIG. 4 shows another organization of the sensors and time periods used by the monitoring system. In this embodiment, the time periods are waking, breakfast, morning activity, lunch, afternoon activity, dinner, and preparation for bed. In this embodiment, the sensors are also grouped by the room that they are positioned, however, in this embodiment, since the activities can take place in more than one room a number of groups of sensors (that have been grouped by room) are combined to create the number of sensor counts for each period.

Figure 5A:
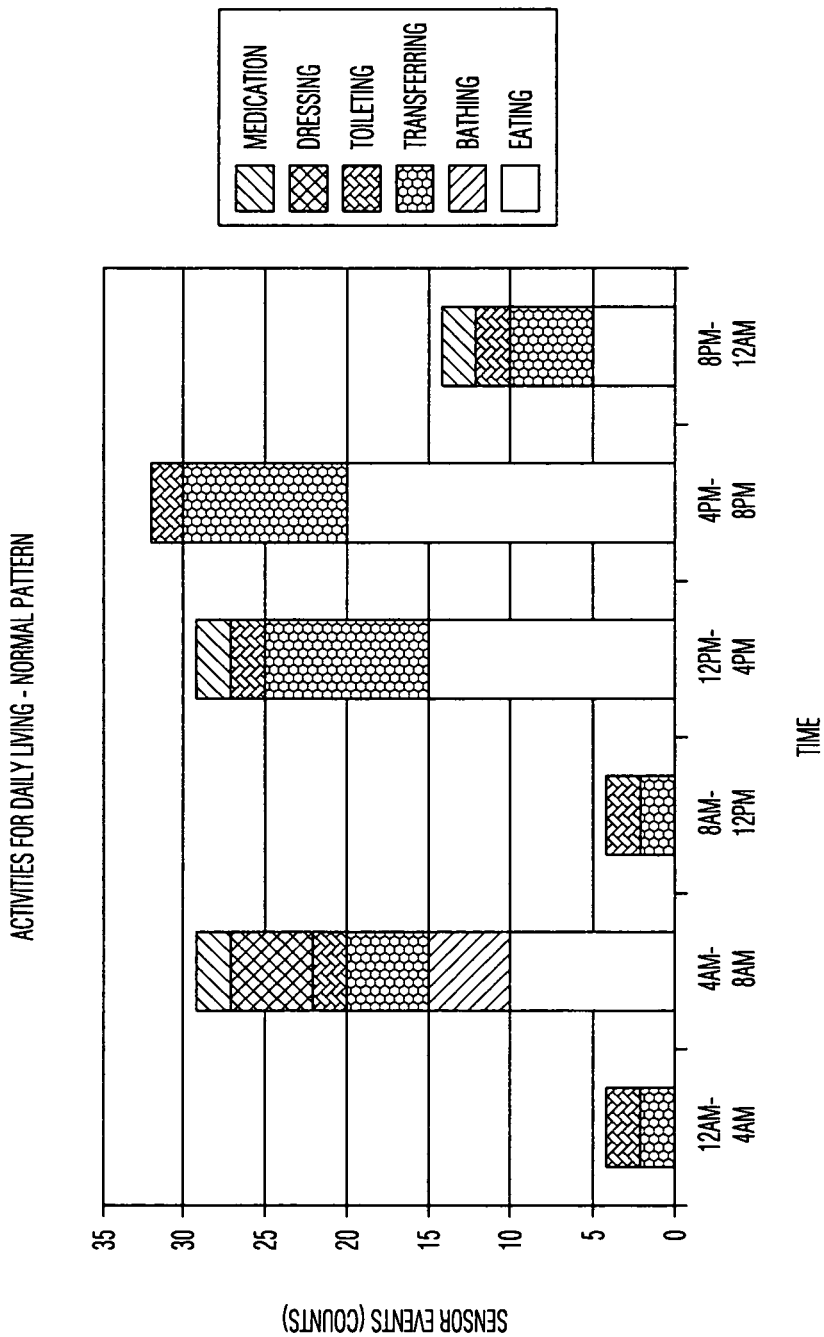
FIG. 5A illustrates examples of sensor counts that can be used in the various embodiments.
Figure 5B:
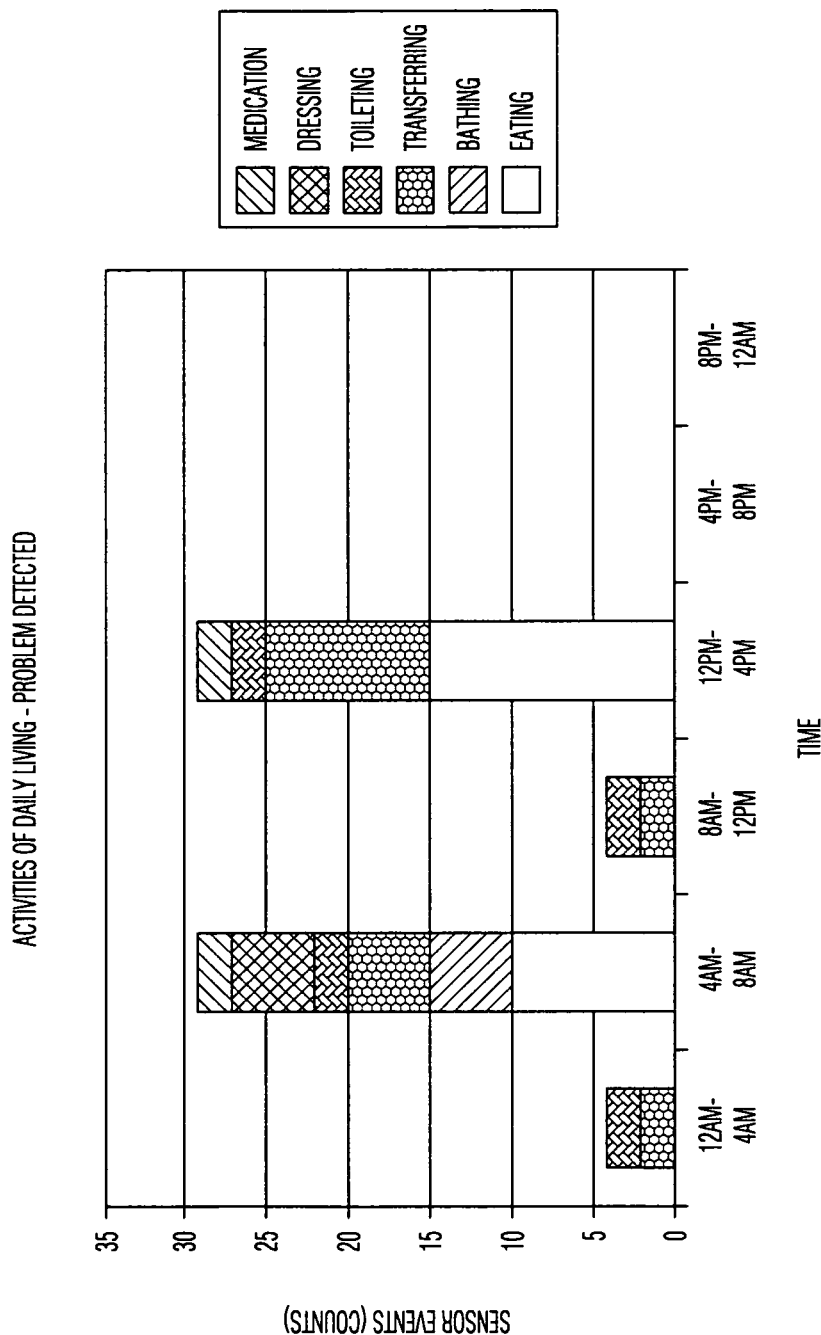
FIG. 5B illustrates examples of sensor counts that can be used in the various embodiments.

FIGS. 5A and 5B illustrate another method of organizing the sensors and time periods for monitoring activity. FIG. 5A illustrates an example of a log of normal counts grouped by time and by an activity of daily living. In this log, the individual is activating sensors in a normal routine.

FIG. 5B illustrates an example of a log of abnormal counts grouped by time and by an activity of daily living. The abnormality can be identified by comparing the log of FIG. 5A with the log of FIG. 5B.

When comparing the two logs it becomes evident that the individual's activity has dropped off to zero for the periods of 4PM-8PM and 8PM-12AM. The program instructions will interpret this statistical change in the counts as a potential situation in which an alert should be issued.

In some embodiments, the individual can wear a sensor to indicate that they are in an area within and/or near the dwelling. Program instructions can check to see if the sensor is located within and/or near to the dwelling. (In some embodiments, the sensor can be detected outside the dwelling, but within a certain range of the transceiver, e.g., transceiver 204).

Locating the wearable sensor can be accomplished in various manners, such as by initiating a ping signal from the transceiver to the wearable sensor. In such a case, the wearable sensor can also include a transceiver and can receive the ping signal and can respond. The transmission of the ping signal can be by any means, such as via a radio frequency, and the like. In some embodiments, the sensor can be constructed to periodically check-in with the monitoring device, such as by sending a ping signal to the monitoring device via radio frequency or other such manner. In such embodiments, the sensor can be provided with energy saving program instructions that allow the sensor to be in "sleep mode," where power usage is reduced, and then to "awaken" periodically to send a ping signal to the monitoring device. Once the signal is sent, the sensor can then return to "sleep mode."

If a response to the ping signal is received by the monitoring device, then the program instructions can interpret that to mean that the individual is within the signal range of the monitoring device. If a deviation in a behavior routine has been identified and a ping response has been received, program instructions can initiate an alert to the individual as has been discussed above. If no response is obtained from the individual, then the program instructions can determine which third party to contact. Those skilled in the art will understand that other sensors can be used in combination with, or instead of, a sensor worn by the individual to determine whether the individual is within the dwelling. Examples of other sensors include, motion sensors, sensors on the interior/exterior/garage doors, and the like.

If the occupant is determined to be away, that decision is recorded along with the evidence supporting the determination. If the occupant is believed to be home, then previously recorded activity can be analyzed to determine the potential activity period.

To determine this period, activities for a number of previous days can be retrieved from memory. The next potential activity period can be selected based on proximity (in time) to the current time (e.g., if it is currently 7AM, those activities nearest to 7AM that happened on previous days will be reviewed first), the frequency with which any activity was observed during that period can be used as the threshold for the current period.

In some embodiments, if trend analysis of the recorded activity indicates that, for example, each day of the week has a distinct pattern, then the system can analyze data from the same day of the week to identify a potential activity period. The decision to trigger an alert is based on two confidence thresholds, for example, that the occupant is home and that the inactivity is anomalous provides a mechanism to reduce the number of false alerts that could potentially be generated.

Additionally, in various embodiments, an emergency switch/button can be used to allow the individual to initiate a call from the third party contact list. For example, the monitoring system can include program instructions to initiate a call to the emergency contact on the call hierarchy when a signal is received from the emergency switch/button.

FIG. 6 illustrates an embodiment of a calling hierarchy. In the embodiment of FIG. 6, the call hierarchy has five contacts thereon. The first contact is to the individual whose activity is being monitored. This contact can be accomplished in any manner, such as by telephone, by displaying a message on the display of the monitoring device, e.g., display 202, by an audible alert that can be turned off through use of the I/O device 206, among others. For example, an audible alert can be a recorded voice that asks the individual to respond to a question, such as, "Are you alright?" The recorded voice can be personalized to have the individual's voice or the voice of a family member ask the question.

If a response is not received within a period of time, the monitoring device, e.g., 101 can initiate a call, such as to the second party on the hierarchical list, in the case of FIG. 6, a neighbor. It is understood that the monitoring system can be designed such that it can skip parties on the hierarchical list under certain circumstances. For example, if the statistical change in the data counts is particularly large, then program instructions can bypass one or more third parties.

Additionally, in various embodiments, based on the type of statistical change, a specific party on the list can be contacted. For example, if the statistical change indicates a drastic drop in eating, program instructions within the monitoring system may analyze the situation through use of logic and decide to initiate a call to the doctor without a call to the neighbor and a family member. The decision by the monitoring system can, for example, be because the individual is indicating a loss of appetite, but is not indicating that the individual has been incapacitated, so there is no need for the neighbor or a family member to check on the individual. However, the doctor may be interested in this information or may be able to provide some assistance in getting the individual to begin eating regularly again.

The embodiment of FIG. 6, also illustrates that the information provided to the third parties can be different such that the third party receives the right amount of information for their needs. For example, since the neighbor is to be asked to check on the individual, the name of the individual and their telephone number are provided along with the request to check on the individual. It is presumed that the neighbor knows where the individual lives, so the address information has not been given. However, the invention is not so limited. The relative receives the same information as the neighbor except the relative also receives the address, since they may have to drive to check on the individual. The doctor and emergency contact receive information regarding the condition that caused the monitoring system to initiate the third party calls, since they may find that information helpful in forming a diagnosis of a health issue. Other information can also be provided, such as driving directions, a list of contacts that have been attempted by the monitoring system, and/or medical history information about the individual, among others.

In various embodiments, the monitoring system includes a transceiver and program instructions to receive a reply from a third party contact that has been contacted. For example, the monitoring system can initiate an alert to a neighbor and the neighbor can call back and reply that they are coming by to check on the individual.

The monitoring system can be programmed to receive the replies in various forms. For example, program instructions can include automated voice response technology to enable the neighbor to speak to the monitoring device and the device can understand the spoken information. In other embodiments, the program instructions can be in the form push button responses from a telephone. However, the invention is not so limited.

Figure 7:
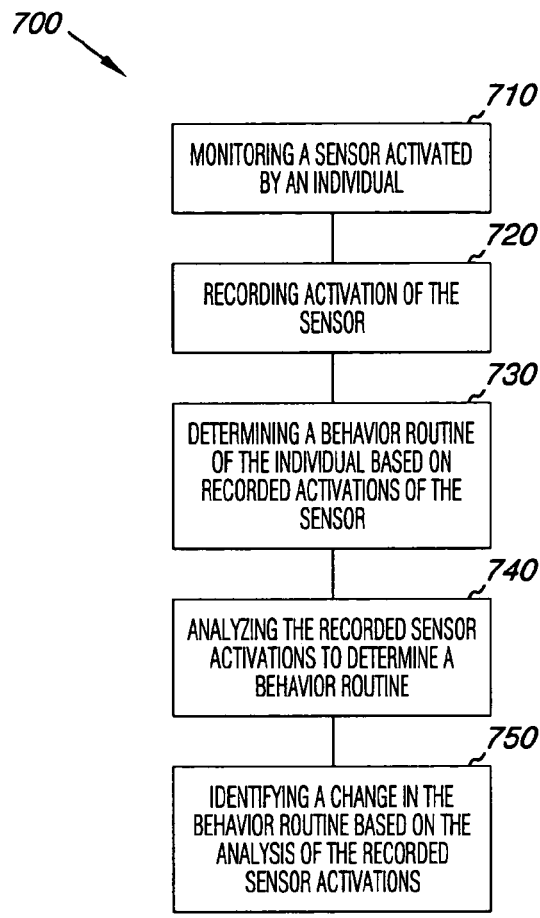
FIG. 7 illustrates a method for monitoring activity.
Figure 8:
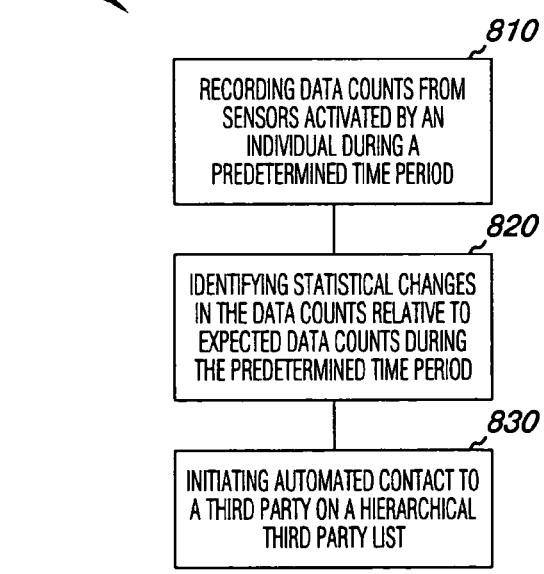
FIG. 8 illustrates another method for monitoring activity.
Figure 9:
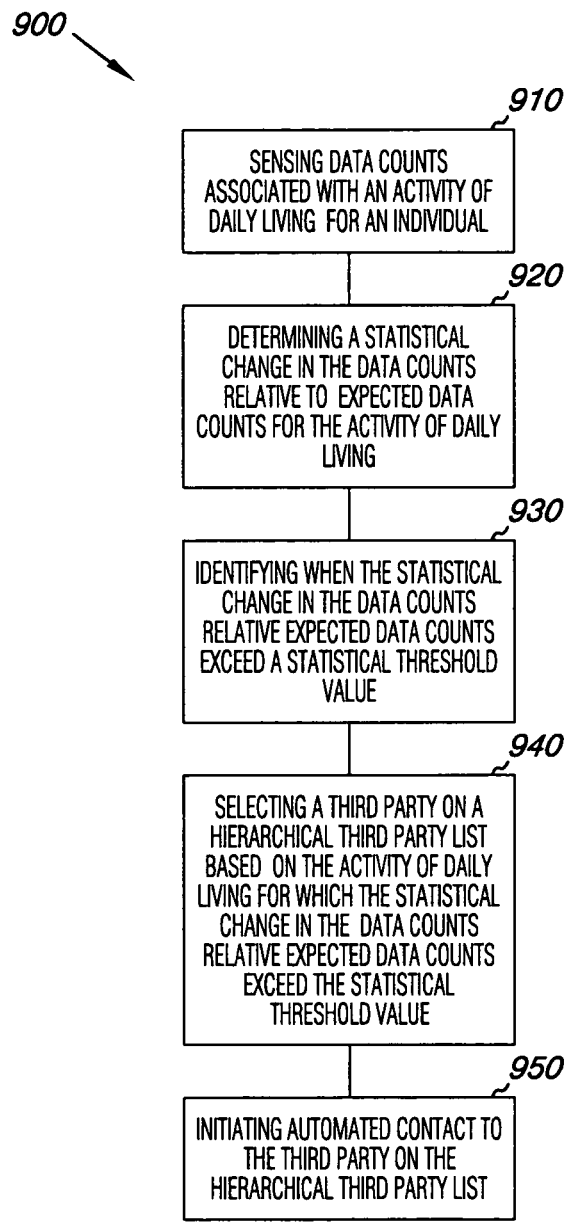
FIG. 9 illustrates another method for monitoring activity.

FIGS. 7-9 illustrate various method embodiments for monitoring activity. Unless explicitly stated, the method embodiments described herein are not constrained to a particular order or sequence. Additionally, some of the described method embodiments and elements thereof can occur or be performed at the same point in time. Method embodiments can be performed by computer executable instructions on software and/or firmware.

The embodiment of FIG. 7 includes monitoring a sensor activated by an individual at block 710. At block 720 the method includes recording activation of the sensor. The method also includes determining a behavior routine of the individual based on recorded activations of the sensor at block 730. At block 740, the method includes analyzing the recorded sensor activations to determine a behavior routine. Analyzing the recorded sensor activations to determine a behavior routine can include using a pattern recognition algorithm. Using a pattern recognition algorithm can include an algorithm based on a Bayesian decision theory, among others. The method also includes identifying a change in the behavior routine based on the analysis of the recorded sensor activations at block 750. Identifying a change in the at least one behavior can include comparing activations of a group of sensors within a class to a threshold.

The method can also include initiating contact to a third party. In various embodiments, initiating contact to a third party can include initiating contact with a third party on a hierarchical list of third party contacts. Initiating contact with a third party on a hierarchical list can include selecting a third party based on the level of change in the behavior routine. In various embodiments, the contact can include automated contact.

Methods can also include grouping sensors within particular classes of daily activities. Methods can include providing a sensor with a level of priority. In such embodiments, identifying a change in the behavior routine can include weighting sensor activations differently based upon the sensor's level of priority.

The embodiment of FIG. 8 includes recording data counts from sensors activated by an individual during a time period at block 810. Recording data counts from a sensor can include recording data counts from a sensor with Boolean logic.

At block 820, the method includes identifying statistical changes in the data counts relative to expected data counts during the time period. Identifying statistical changes in the data counts can include developing an expected count for the activity of daily living over the time period and initiating automated contact to a third party on the hierarchical third party list when the recorded counts are statistically less than the expected count for the activity of daily living over the time period.

The method also includes initiating automated contact to a third party on a hierarchical third party list identified by the individual when a statistical change exceeds a statistical threshold value at block 830. Initiating automated contact to a third party on a hierarchical third party list can include analyzing the data counts in a group for a statistical change that exceeds the statistical threshold value. Initiating automated contact to a third party on a hierarchical third party list can include identifying at least two statistical based changes that exceed the statistical threshold value. Initiating automated contact to a third party on a hierarchical third party list includes prompting the individual to confirm that automated contact to the third party should be made.

In various embodiments, methods can also include associating the data count with an activity of daily living and placing the data counts into groups based on activities of daily living. Methods can also include setting the time period to a value of one (1) hour or greater, however, the invention is not so limited. Methods can also include diagnosing an operational condition of a sensor that detected a reduced number of data counts.

The embodiment of FIG. 9 includes sensing data counts associated with an activity of daily living for an individual at block 910. At block 920, the method includes determining a statistical change in the data counts relative to expected data counts for the activity of daily living.

The method also includes identifying when the statistical change in the data counts relative expected data counts exceed a statistical threshold value at block 930. At block 940, the method includes selecting a third party on a hierarchical third party list prepared by the individual based on the activity of daily living for which the statistical change in the data counts relative expected data counts exceed the statistical threshold value.

The method includes initiating automated contact to the third party on the hierarchical third party list when the statistical based change exceeds the statistical threshold value at block 950. Initiating automated contact to a third party on a hierarchical third party list can also include prompting the individual to confirm that automated contact to the third party should be made.

In various embodiments, methods can also include adjusting the expected data counts of an activity of daily living based upon the statistical change in the data counts for the activity of daily living. Methods can also include providing a predetermined amount of information about the individual and the activity of daily living to the third party on the hierarchical third party list. Methods can also include placing the third parties on the hierarchical third party list into multiple tiers of contacts. In such embodiments, selecting the third party on the hierarchical third party list can also include selecting a second third party in a next tier of the multiple tiers.

Methods can also include requesting automated contact to the third party on the hierarchical third party list by the individual and initiating the automated contact to the third party on the hierarchical third party list at the request of the individual. In various embodiments, the method can also include identifying a sensor that is not transmitting data counts based on the statistical change in the data counts of the sensor relative to expected data counts for the sensor. Methods can also include adjusting the expected data counts for the sensor based upon the statistical change in the data counts.

Although specific embodiments have been illustrated and described herein, those of ordinary skill in the art will appreciate that an arrangement calculated to achieve the same techniques can be substituted for the specific embodiments shown. As one of ordinary skill in the art will appreciate upon reading this disclosure, various embodiments of the invention can be performed in one or more devices, device types, and system environments including networked environments.

Combination of the above embodiments, and other embodiments not specifically described herein will be apparent to those of skill in the art upon reviewing the above description. The scope of the various embodiments of the invention includes other applications in which the above structures and methods can be used. Therefore, the scope of various embodiments of the invention should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method for monitoring activity, comprising:
    monitoring, by a computing device having a computer processor and computer-readable code stored on a computer-readable medium and executable by the computer processor, a number of sensors activated by an individual, wherein the number of sensors are located in a dwelling of the individual;
    recording activations of the number of sensors on the computing device in communication with the number of sensors;
    determining a behavior routine of the individual with the computing device based on recorded activations of the number of sensors, wherein a number of patterns of a number of sensor activations are identified that indicate the individual performing a number of activities that make up the behavior routine;
    identifying a statistical change in the behavior routine with the computing device based on an analysis of the recorded sensor activations, wherein the analysis includes a comparison of the recorded sensor activations to a threshold;
    determining, with the computing device, a confidence level of the identification of the change in the behavior routine, wherein the confidence level is based on the analysis of the statistical changes in the data counts relative to expected data counts of sensor activations of a first group of the number of sensors with sensor activations of one or more groups of the number of sensors and wherein the confidence level provides a level of certainty that the change in the statistical changes in the data counts relative to expected data counts have exceeded a statistical threshold value; and
    initiating contact to a third party on a hierarchical list of third party contacts with the computing device in response to identifying the change in the behavior routine, wherein the third party on the hierarchical list to contact is selected based on a level of change in the behaviour routine and the confidence level.

2. The method of claim 1, further including initiating automated contact with a third party on a hierarchical list of third party contacts.

3. The method of claim 1, further including grouping sensors within particular classes of daily activities.

4. The method of claim 3, wherein identifying a change in the behavior routine includes comparing activations of a group of sensors within a class to a threshold.

5. The method of claim 1, wherein the method further includes providing a sensor with a level of priority.

6. The method of claim 5, wherein identifying a change in the behavior routine includes weighting sensor activations differently based upon the sensor's level of priority.

7. The method of claim 6, wherein determining the behavior routine includes using a pattern recognition algorithm.

8. The method of claim 7, wherein using a pattern recognition algorithm includes using an algorithm based on a Bayesian decision theory.

9. A method for monitoring the behavior of an individual, comprising:
    recording, by a computing device having a computer processor and computer-readable code stored on a computer-readable medium and executable by the computer processor, data counts from a number of sensors activated by an individual during a time period on the computing device in communication with the number of sensors to determine a behavior routine of the individual, wherein the number of sensors are located in a dwelling of the individual and a number of patterns of the data counts are identified that indicate the individual performing a number of activities that make up the behavior routine;

identifying statistical changes in the data counts relative to expected data counts during the time period with the computing device;

determining, with the computing device, a confidence level of the statistical changes in the data counts relative to expected data counts based on the statistical changes in the data counts relative to expected data counts and a comparison of data counts from a first group of the number of sensors with data counts from one or more groups of the number of sensors, wherein the confidence level provides a level of certainty that the statistical changes in the data counts relative to expected data counts have exceeded a statistical threshold value; and initiating automated contact to a third party on a hierarchical third party list with the computing device identified by the individual when a statistical change exceeds the statistical threshold value, wherein the third party on the hierarchical list to contact is selected based on a level of statistical change and the confidence level.

10. The method of claim 9, further including:
associating the data counts with an activity of daily living; and
placing the data counts into groups based on activities of daily living.

11. The method of claim 10, wherein initiating automated contact to a third party on a hierarchical third party list includes analyzing the data counts in a group for a statistical change that exceeds the statistical threshold value.

12. The method of claim 10, wherein identifying statistical changes in the data counts includes:
developing an expected count for the activity of daily living over the time period; and
initiating automated contact to a third party on the hierarchical third party list when the recorded counts are statistically less than the expected count for the activity of daily living over the time period.

13. The method of claim 9, further including setting the time period to a value of one (1) hour or greater.

14. The method of claim 9, wherein initiating automated contact to a third party on a hierarchical third party list includes identifying at least two statistical based changes that exceed the statistical threshold value.

15. The method of claim 9, wherein recording data counts from a sensor includes recording data counts from a sensor with Boolean logic.

16. The method of claim 9, further including self-diagnosing an operational condition of a monitoring system based on the recorded data counts.

17. The method of claim 16, further including diagnosing an operational condition of a sensor in the monitoring system.

18. The method of claim 9, wherein initiating automated contact to a third party on a hierarchical third party list includes prompting the individual to confirm that automated contact to the third party should be made.

19. A computer readable medium having a program to cause a device to perform a method, comprising:
sensing data counts associated with a number of activities of daily living for an individual, wherein the data counts are from activations of a number of sensors that are located in a dwelling of an individual;
determining a behavior routine of the individual based on the sensed data counts, wherein a number of patterns of the sensed data counts are identified that indicate the individual performing the number of activities of daily living that make up the behavior routine;
determining a statistical change in the data counts relative to expected data counts for the activity of daily living;
identifying when the statistical change in the data counts relative expected data counts exceed a statistical threshold value;
determining a confidence level of the statistical change in the data counts relative expected data counts based on the statistical change in the data counts relative to expected data counts and a comparison of data counts from a first group of the number of sensors with data counts from one or more groups of the number of sensors, wherein the confidence level of the statistical change provides a level of certainty that the statistical change has exceeded the statistical threshold value;
selecting a third party on a hierarchical third party list based on the activity of daily living for which the statistical change in the data counts relative expected data counts exceed the statistical threshold value, a level of statistical change in the data counts, and the confidence level; and
initiating automated contact to the third party on the hierarchical third party list when the statistical based change exceeds the statistical threshold value.

20. The method of claim 19, further including adjusting the expected data counts of the number of activities of daily living based upon the statistical change in the data counts for the activity of daily living.

21. The method of claim 19, further including providing a predetermined amount of information about the individual and the number of activities of daily living to the third party on the hierarchical third party list.

22. The method of claim 19, wherein the initiating automated contact to a third party on a hierarchical third party list further includes prompting the individual to confirm that automated contact to the third party should be made.

23. The method of claim 19, further including placing the third party contacts in tiers of third party contacts wherein at least one tier includes multiple third party contacts.

24. The method of claim 19, further including:
requesting automated contact to the third party on the hierarchical third party list by the individual; and
initiating the automated contact to the third party on the hierarchical third party list at the request of the individual.

25. The method of claim 19, further including identifying a sensor that is not transmitting data counts based on the statistical change in the data counts of the sensor relative to expected data counts for the sensor.

26. The method of claim 25, further including adjusting the expected data counts for the sensor based upon the statistical change in the data counts.

27. A system to monitoring activity, comprising:
means for signaling that a number of sensors have been activated by an individual during activities of daily living, wherein the number of sensors include sensors located in a dwelling of the individual;
a receiver to receive signals, indicating that the number of sensors have been activated;
a tabulation unit including a computing device to tabulate the number of received signals;
an analysis unit including a computing device to analyze the statistical tabulated signals to determine a behavior routine, identify changes in the behavior routine, and determine a confidence level of the identified changes in the behavior routine based on the changes in the behavior routine and a comparison of the number of received signals from a first group of the number of sensors with the number of received signals from one or more groups of the number of sensors, wherein the confidence level provides a level of certainty that the statistical changes in the behavior routine occurred and wherein a number of patterns of a number of sensor activations are identified that indicate the individual performing the activities of daily living that make up the behavior routine; and a contacting unit including a computing device to initiate contact with a third party selected from a hierarchical list of third party contacts when the analysis unit identifies a defined level change in the behavior routine.

28. The system of claim 27, wherein means for signaling includes a sensor worn by the individual.

29. The system of claim 28, wherein the sensor worn by the individual is a sensor that is actuated when the sensor is located within a range that includes the dwelling and a portion of land on which the dwelling is situated.

30. The system of claim 27, wherein means for signaling includes digital sensors.

31. The system of claim 27, wherein the means for signaling includes analog sensors.

32. The system of claim 31, wherein the analog sensors produce a Boolean output.

33. A device for monitoring activity, comprising:

a receiver to receive activation signals from a number of sensors activated by an individual during activities of daily living, wherein the number of sensors include sensors located in a dwelling of the individual;

a processing unit including a computing device to tabulate the received signals to determine a behavior routine, identify changes in the behavior routine, and determine a confidence level of the identified changes in the behavior routine based on the statistical changes and a comparison of the number of received signals from a first group of the number of sensors with the number of received signals from one or more groups of the number of sensors, wherein the confidence level provides a level of certainty that the statistical changes in the behavior routine occurred and wherein a number of patterns of the received activation signals are identified that indicate the individual performing the activities of daily living that make up a behavior routine; and a contacting unit to initiate contact with a third party selected from a hierarchical list of third party contacts based on a defined level of change in a behavior routine and the confidence level when directed by the processing unit.

34. The device of claim 33, wherein the device is a self contained, stand-alone device.

35. The device of claim 34, wherein the device includes an additional functionality selected from: a radio, a clock radio, an alarm clock, a telephone, and an answering machine.

* * * * *